(12) United States Patent
Enari

(10) Patent No.: US 11,832,972 B2
(45) Date of Patent: Dec. 5, 2023

(54) BIOLOGICAL ANALYSIS DEVICE, BIOLOGICAL ANALYSIS METHOD, AND PROGRAM

(71) Applicant: SEIKO EPSON CORPORATION, Tokyo (JP)

(72) Inventor: Megumi Enari, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 1237 days.

(21) Appl. No.: 16/164,104

(22) Filed: Oct. 18, 2018

(65) Prior Publication Data

US 2019/0117171 A1 Apr. 25, 2019

(30) Foreign Application Priority Data

Oct. 19, 2017 (JP) ................. 2017-202432

(51) Int. Cl.
| | |
|---|---|
| *A61B 5/00* | (2006.01) |
| *A61B 5/021* | (2006.01) |
| *A61B 5/026* | (2006.01) |
| *A61B 5/024* | (2006.01) |

(52) U.S. Cl.
CPC .......... *A61B 5/7278* (2013.01); *A61B 5/0261* (2013.01); *A61B 5/02108* (2013.01); *A61B 5/02438* (2013.01); *A61B 5/681* (2013.01)

(58) Field of Classification Search
CPC .............. A61B 5/7278; A61B 5/02108; A61B 5/02438; A61B 5/0261; A61B 5/681
See application file for complete search history.

(56) References Cited

U.S. PATENT DOCUMENTS

| | | | |
|---|---|---|---|
| 2017/0209055 A1* | 7/2017 | Pantelopoulos | ..... A61B 5/7203 |
| 2017/0231553 A1 | 8/2017 | Igarashi et al. | |
| 2017/0251930 A1 | 9/2017 | Machida et al. | |
| | (Continued) | | |

FOREIGN PATENT DOCUMENTS

| | | |
|---|---|---|
| JP | 2004-154231 A | 6/2004 |
| JP | 2008-018035 A | 1/2008 |
| JP | 2014-079428 A | 5/2014 |
| | (Continued) | |

OTHER PUBLICATIONS

Masaki Goma et al., "The Development of Small Laser Doppler Blood Flow Sensor", Pioneer R&D, vol. 21, No. 1, pp. 30-37, 2012.

*Primary Examiner* — Patrick Fernandes
*Assistant Examiner* — Joseph A Tombers
(74) *Attorney, Agent, or Firm* — Oliff PLC

(57) ABSTRACT

A biological analysis device includes a CPU as a control device which determines a boundary between a first bandwidth in which a temporal change in a signal intensity is large and a second bandwidth which is located closer to a high frequency side than the first bandwidth and in which a temporal change in the signal intensity is less than the first bandwidth in a plurality of intensity spectra related to frequencies calculated sequentially with regard to light reflected and received inside a biological body through radiation of a laser beam, and calculates a biological index related to a blood flow of the biological body from a signal intensity within a frequency range in which the boundary is an upper limit in the intensity spectrum.

9 Claims, 6 Drawing Sheets

(56) References Cited

U.S. PATENT DOCUMENTS

2018/0008152 A1* 1/2018 Watanabe ............... G01F 1/663
2020/0170569 A1* 6/2020 Watanabe .............. A61B 10/00

FOREIGN PATENT DOCUMENTS

| JP | 6095863 B1 | 3/2017 |
| JP | 2017-153875 A | 9/2017 |
| WO | 2015/199159 A1 | 12/2015 |

* cited by examiner

BIOLOGICAL ANALYSIS DEVICE, BIOLOGICAL ANALYSIS METHOD, AND PROGRAM

BACKGROUND

1. Technical Field

The present invention relates to a technology for analyzing a state of a biological body.

2. Related Art

Technologies for calculating indexes related to states of biological bodies have been proposed in the related art. For example, JP-A-2014-79428 discloses a configuration in which a blood flow signal is generated by receiving scattered light arriving from a biological body at the time of radiating a laser beam and a blood flow in the biological body is calculated using a power spectrum of the blood flow signal. The blood flow is calculated using a portion within a specific frequency range in the power spectrum of the blood flow signal. An upper limit of the frequency range used in the calculation of the blood flow is set in advance in a frequency corresponding to a predetermined threshold in the power spectrum.

However, when a preset fixed value is set as the threshold as in the technology of JP-A-2014-79428, a blood flow in which a component indicating a beat of a biological body in the blood flow signal is appropriately reflected may not be calculated in some cases.

SUMMARY

An advantage of some aspects of the invention is to calculate an appropriate biological index in which a beat of a biological body is reflected.

A biological analysis device according to a preferred aspect of the invention includes a boundary determination unit that determines a boundary between a first bandwidth in which a temporal change in a signal intensity is large and a second bandwidth which is located closer to a high frequency side than the first bandwidth and in which a temporal change in the signal intensity is less than the first bandwidth in a plurality of intensity spectra related to frequencies calculated sequentially with regard to light reflected and received inside a biological body through radiation of a laser beam; and a biological analysis unit that calculates a biological index related to a blood flow of the biological body from a signal intensity within a frequency range in which the boundary is an upper limit in the intensity spectrum. In the aspect, the biological index is calculated from the intensity within the frequency range in which the boundary between the first bandwidth in which the temporal change in the signal intensity is large and the second bandwidth which is located closer to the high frequency side than the first bandwidth and in which the temporal change in the signal intensity is less than the first bandwidth in the intensity spectra related to the frequencies calculated sequentially with regard to the light reflected and received inside the biological body through radiation of the laser beam. Accordingly, compared to a configuration in which a biological index is calculated from the intensity within a frequency range in which a portion other than the boundary between the first and second bandwidths is an upper limit, it is possible to calculate a more appropriate biological index in which a beat of the biological body is reflected.

In the preferred aspect of the invention, the biological analysis device may further include a change calculation unit that calculates a change index which is an index of a temporal change quantity of a signal intensity for each frequency in the plurality of intensity spectra. The boundary determination unit may determine the boundary in accordance with the change index. In the aspect with this configuration, it is possible to appropriately determine the boundary between the first and second bandwidths in accordance with the change index which is the index of the temporal change quantity of the signal intensity for each frequency in the plurality of intensity spectra.

In the preferred aspect of the invention, the change calculation unit may calculate the change index in accordance with a difference in a signal intensity between an intensity spectrum at a first time point at which a beat index interlocking with a beat of the biological body is maximum within a predetermined period and an intensity spectrum at a second time point at which the beat index interlocking with the beat of the biological body is minimum within the predetermined period among the plurality of intensity spectra. In the aspect with this configuration, the change index is calculated in accordance with the difference in the signal intensity between the intensity spectrum at the first time point at which the beat index is maximum within the predetermined period and the intensity spectrum at the second time point at which the beat index is minimum within the predetermined period. Therefore, compared to a configuration in which the change index is calculated in accordance with a difference in the signal intensity between two intensity spectra at two time points selected irrespective of magnitude of the beat index, it is possible to calculate the change index in which the difference in the signal intensity between the two intensity spectra is appropriately reflected.

In the preferred aspect of the invention, the predetermined period may be equal to or greater than 0.5 seconds and equal to or less than 2 seconds. In the aspect with this configuration, the change index in the intensity spectrum between the first time point at which the beat index is maximum and the second time point at which the beat index is minimum is calculated within the period equal to or greater than 0.5 seconds and equal to or less than 2 seconds. For example, compared to a configuration in which the predetermined period is shorter than 0.5 seconds, it is possible to calculate the change index in which an influence of a beat of a biological body is appropriately reflected.

In the preferred aspect of the invention, the change calculation unit may calculate the change index by dividing the difference in the signal intensity between the intensity spectrum at the first time point and the intensity spectrum at the second time point by an average of signal intensities between the intensity spectrum at the first time point and the intensity spectrum at the second time point. In the aspect with this configuration, the change index is calculated by dividing the difference in the signal intensity between the intensity spectrum at the first time point and the intensity spectrum at the second time point by the average of signal intensities between the intensity spectrum at the first time point and the intensity spectrum at the second time point. Therefore, an influence in which the signal intensity is smaller on a high frequency side is reduced. Accordingly, compared to a configuration in which a difference in the signal intensity between the intensity spectrum at the first time point and the intensity spectrum at the second time point is calculated as the change index, it is possible to calculate the change index in which a temporal change in the signal intensity is more predominantly reflected.

In the preferred aspect of the invention, the change calculation unit may calculate the change index in accordance with a degree of scattering of the signal intensity for each frequency in the plurality of intensity spectra. In the aspect with this configuration, it is possible to appropriately calculate the change index in accordance with the degree of scattering of the signal intensity in the plurality of intensity spectra.

In the preferred aspect of the invention, the change calculation unit may calculate the change index by dividing a standard deviation or a dispersion of the signal intensity for each frequency in the plurality of intensity spectra by the average of the signal intensities between the plurality of intensity spectra. In the aspect with this configuration, the change index is calculated by dividing the standard deviation or the dispersion of the signal intensity for each frequency in the plurality of intensity spectra by the average of the signal intensities between the plurality of intensity spectra. Therefore, an influence in which the signal intensity is smaller on a high frequency side is reduced. Accordingly, compared to a configuration in which the standard deviation or the dispersion of the signal intensity for each frequency in the plurality of intensity spectra is calculated as the change index, it is possible to calculate the change index in which a temporal change in the signal intensity is more predominantly reflected.

In the preferred aspect of the invention, the biological index may be a blood quantity index obtained by integrating intensities in the intensity spectrum within the frequency range.

In the preferred aspect of the invention, the biological index may be a blood flow index obtained by integrating a product of an intensity of each frequency in the intensity spectrum and the frequency within the frequency range.

In the preferred aspect of the invention, the biological analysis device may further include a blood pressure calculation unit that calculates a blood pressure index related to a blood pressure of the biological body from the biological index. In the aspect with this configuration, there is the advantage that the blood pressure index related to the blood pressure which is a basic and important index for diagnosing a state of a biological body can be calculated.

A biological analysis method according to a preferred aspect of the invention includes: determining a boundary between a first bandwidth in which a temporal change in a signal intensity is large and a second bandwidth which is located closer to a high frequency side than the first bandwidth and in which a temporal change in the signal intensity is less than the first bandwidth in a plurality of intensity spectra related to frequencies calculated sequentially with regard to light reflected and received inside a biological body through radiation of a laser beam; and calculating a biological index related to a blood flow of the biological body from a signal intensity within a frequency range in which the boundary is an upper limit in the intensity spectrum.

A program according to a preferred aspect of the invention causes a computer to function as: a boundary determination unit that determines a boundary between a first bandwidth in which a temporal change in a signal intensity is large and a second bandwidth which is located closer to a high frequency side than the first bandwidth and in which a temporal change in the signal intensity is less than the first bandwidth in a plurality of intensity spectra related to frequencies calculated sequentially with regard to light reflected and received inside a biological body through radiation of a laser beam; and a biological analysis unit that calculates a biological index related to a blood flow of the biological body from a signal intensity within a frequency range in which the boundary is an upper limit in the intensity spectrum.

BRIEF DESCRIPTION OF THE DRAWINGS

The invention will be described with reference to the accompanying drawings, wherein like numbers reference like elements.

FIG. 2 is a diagram illustrating a configuration in which a function of the biological analysis device is focused on.

FIG. 3 is a diagram illustrating a configuration in which a function of a control device is focused on.

DESCRIPTION OF EXEMPLARY EMBODIMENTS

First Embodiment

Figure 1:
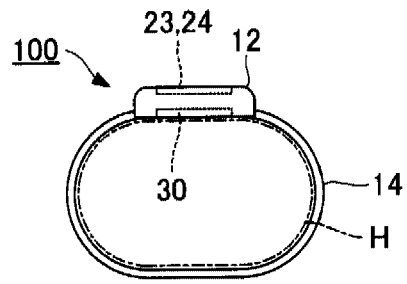
FIG. 1 is a side view illustrating a biological analysis device according to a first embodiment of the invention.

FIG. 1 is a side view illustrating a biological analysis device 100 according to a first embodiment of the invention. The biological analysis device 100 is a measurement instrument that measures biological information of a subject in a non-invasive manner. The biological analysis device 100 according to the first embodiment measures a blood pressure of a specific part (hereinafter referred to as a "measurement part") H of the body of a subject as biological information. In the following description, a wrist or an upper arm of the subject is exemplified as the measurement part H.

The biological analysis device 100 is worn on the measurement part H. As exemplified in FIG. 1, the biological analysis device 100 according to the first embodiment is a wrist-watch type portable device including a casing 12 and a belt 14. The biological analysis device 100 is worn on the body of the subject by winding the belt 14 around the measurement part H.

Figure 2:
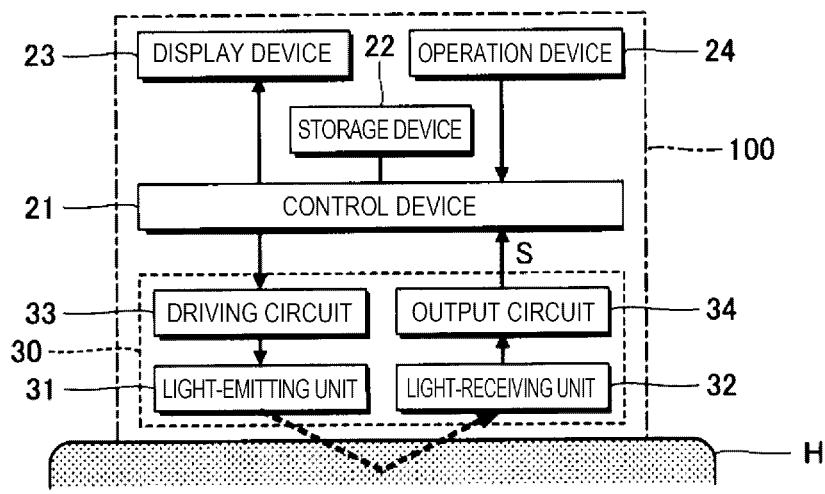

FIG. 2 is a diagram illustrating an electric configuration of the biological analysis device 100. As exemplified in FIG. 2, the biological analysis device 100 according to the first embodiment includes a control device 21, a storage device 22, a display device 23, an operation device 24, and a detection device 30. The control device 21 and the storage device 22 are installed inside the casing 12.

The display device 23 (for example, a liquid crystal display panel) and the operation device 24 are installed on, for example, a surface of the casing 12 opposite to the measurement part H, as exemplified in FIG. 1. The display device 23 displays various images including a measurement result under the control of the control device 21. The operation device 24 is an input device that receives an instruction from the user. For example, a plurality of operators operated by the user or a touch panel on which a touch on a display surface of the display device 23 by the user is detected is appropriate as the operation device 24.

The detection device 30 is an optical sensor module that generates a detection signal S in accordance with a state of the measurement part H. As exemplified in FIG. 2, the detection device 30 according to the first embodiment includes a light-emitting unit 31, a light-receiving unit 32, a driving circuit 33, and an output circuit 34. The light-emitting unit 31 and the light-receiving unit 32 are installed at, for example, positions (generally, a surface in contact with the measurement part H) of the casing 12 facing the measurement part H. One or both of the driving circuits 33 and the output circuit 34 can also be installed as an external circuit separate from the detection device 30.

The light-emitting unit 31 is a light source that radiates light to the measurement part H. The light-emitting unit 31 according to the first embodiment radiates a coherent laser beam to the measurement part H with a narrowband. For example, a light-emitting element such as a vertical cavity surface emitting LASER (VCSEL) that emits a laser beam by resonance in a resonator is used appropriately as the light-emitting unit 31. The light-emitting unit 31 according to the first embodiment radiates, for example, light with a predetermined wavelength $\lambda$ ($\lambda$=800 nm to 1300 nm) in a near infrared area to the measurement part H. The driving circuit 33 in FIG. 2 causes the light-emitting unit 31 to emit the light under the control of the control device 21. A plurality of light-emitting elements emitting light with different wavelengths may be used as the light-emitting unit 31. The light emitted by the light-emitting unit 31 is not limited to the near infrared light.

Light incident on the measurement part H from the light-emitting unit 31 is repeatedly diffused and reflected while passing inside the measurement part H to exit to the side of the casing 12. Specifically, the light passing through a blood vessel such as an artery (for example, a brachial artery, a radial artery, or an ulnar artery) inside the measurement part H and blood in the blood vessel exits from the measurement part H to the side of the casing 12. The light-receiving unit 32 receives the light arriving from the measurement part H. For example, a light-receiving element such as a photodiode (PD) that generates charges in accordance with the light reception intensity is used as the light-receiving unit 32. Specifically, a light-receiving element in which a photoelectric conversion layer is formed of indium, gallium, and arsenic (InGaAs) having high sensitivity in a near infrared area is appropriate as the light-receiving unit 32. As understood from the above description, the detection device 30 according to the first embodiment is a reflective optical sensor in which the light-emitting unit 31 and the light-receiving unit 32 are located on one side of the measurement part H. Here, a transmissive optical sensor in which the light-emitting unit 31 and the light-receiving unit 32 are located on opposite sides with the measurement part H interposed therebetween may be used as the detection device 30.

The output circuit 34 generates a detection signal S in accordance with the intensity of the light received by the light-receiving unit 32. Specifically, the output circuit 34 includes an amplification circuit (not illustrated) that generates an output signal with a voltage in accordance with the charges generated by the light-receiving unit 32 and an A/D converter (not illustrate) that generates a detection signal S by converting the output signal by the amplification circuit from an analog signal into a digital signal. The detection signal S generated by the output circuit 34 is supplied to the control device 21.

The light arriving at the light-receiving unit 32 includes a component diffused and reflected from a tissue (a stationary tissue) stationary inside the measurement part H and a component diffused and reflected from an object (generally, a red blood cell) moving inside an artery inside the measurement part H. The frequency of light before and after the diffusion and reflection from a stationary tissue is not changed. However, before and after diffusion and reflection from a red blood cell, the frequency of light is changed by a change quantity (hereinafter referred to as a "frequency shift quantity") proportional to a movement speed (that is, a blood flow rate) of the red blood cell. That is, the light passing through the measurement part H and arriving at the light-receiving unit 32 contains a component that is changed (frequency-shifted) by the frequency shift quantity with respect to the frequency of the light emitted by the light-emitting unit 31. The detection signal S supplied to the control device 21 is an optical beat signal in which the frequency shift by a blood flow inside the measurement part H is reflected.

The control device 21 in FIG. 2 is an arithmetic processing device such as a central processing unit (CPU) or a field-programmable gate array (FPGA) and controls the whole biological analysis device 100. The storage device 22 includes, for example, a nonvolatile semiconductor memory and stores a program to be executed by the control device 21 and various kinds of data to be used by the control device 21. A configuration in which functions of the control device 21 are distributed to a plurality of integrated circuits can be adopted or a configuration in which some or all of the functions of the control device 21 are realized by a dedicated electronic circuit can also be adopted. In FIG. 2, the control device 21 and the storage device 22 are illustrated as separate elements, but the control device 21 containing the storage device 22 can also be realized by, for example, an application specific integrated circuit (ASIC) or the like.

Figure 3:
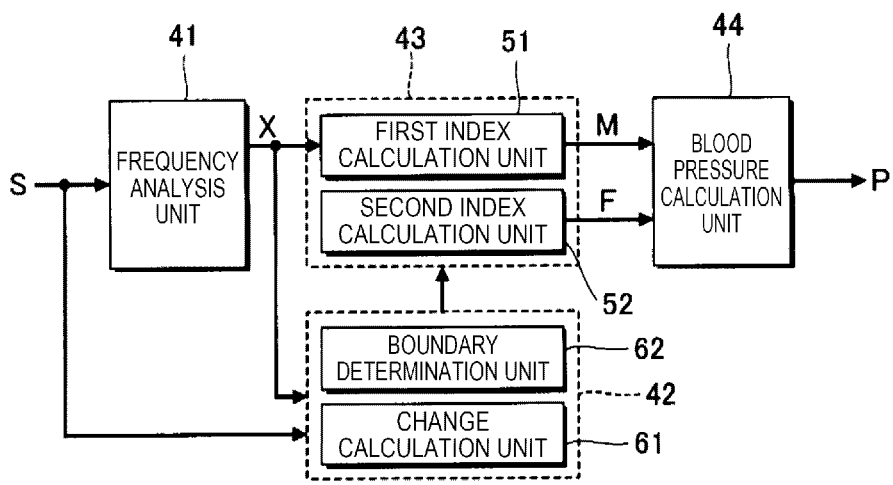

FIG. 3 is a diagram illustrating a configuration in which a function of the control device 21 according to the first embodiment is focused on. The control device 21 according to the first embodiment realizes a plurality of functions (a frequency analysis unit 41, a range setting unit 42, a biological analysis unit 43, and a blood pressure calculation unit 44) of calculating a blood pressure P of a biological body from the detection signal S generated by the detection device 30 by executing a program stored in the storage device 22. Some of the functions of the control device 21 may be realized by a dedicated electronic circuit.

Figure 4:
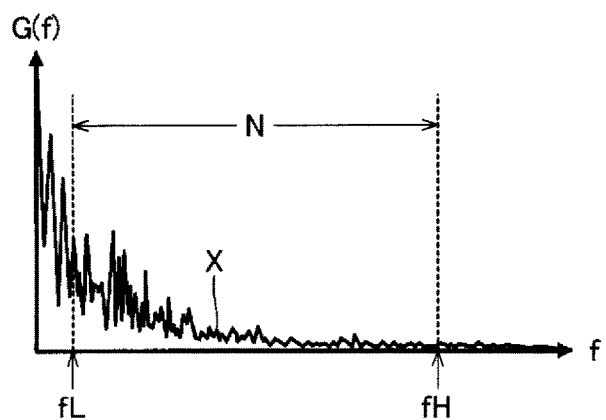
FIG. 4 is a graph illustrating an intensity spectrum.

The frequency analysis unit 41 in FIG. 3 calculates an intensity spectrum (for example, a power spectrum) X related to a frequency from the detection signal S. The intensity spectrum X is a distribution of a signal intensity (power or amplitude) G(f) of a signal component of the detection signal S at each frequency (Doppler frequency) f, as exemplified in FIG. 4. In the calculation of the intensity spectrum X, any known frequency analysis such as fast Fourier transform (FFT) can be adopted. The calculation of the intensity spectrum X by the frequency analysis unit 41 is repeatedly executed for each unit time (frame) on a time axis. The unit period is a period that is sufficiently shorter than a period (hereinafter referred to as a "beat period") T equivalent to one of beats of a heart. The beat period T has a time length, for example, equal to or greater than 0.5 seconds less than 2 seconds. Any two unit periods before and after a phase on the time axis overlap each other. As understood from the foregoing description, the intensity spectrum X of light reflected and received inside a biological body through radiation of a laser beam is sequentially calculated.

The range setting unit 42 in FIG. 3 sets a specific range on a frequency axis (hereinafter referred to as a "frequency range") N. As exemplified in FIG. 4, the frequency range N is a range between a lower limit fL and an upper limit fH on the frequency axis. The lower limit fL is less than the upper limit fH. The setting of the frequency range N by the range setting unit 42 will be described below.

The biological analysis unit 43 in FIG. 3 calculates an index related to a blood flow of a biological body (hereinafter referred to as a "biological index") from the signal intensity G(f) of a signal component within the frequency range N set by the range setting unit 42 in the intensity spectrum X calculated by the frequency analysis unit 41. The biological analysis unit 43 according to the first embodiment calculates each of the blood quantity index M and the blood flow index F as a biological index. As understood from the foregoing description, the frequency range N set by the range setting unit 42 is a frequency bandwidth used to calculate a biological index of the measurement part H in the intensity spectrum X. The biological analysis unit 43 according to the first embodiment includes a first index calculation unit 51 and a second index calculation unit 52.

The first index calculation unit 51 calculates a blood quantity index M (so-called MASS value) from the signal intensity G(f) of the signal component within the frequency range N in the intensity spectrum X. The blood quantity index M is an index of a blood quantity (specifically, the number of red blood cells in a unit volume) of the measurement part H. A blood quantity is changed in conjunction with pulsation of a blood vessel diameter synchronized with a beat of a heart. That is, the blood quantity index M also correlates with a blood vessel diameter. Accordingly, the blood quantity index M can be paraphrased as an index of a blood vessel diameter (further, a unit area of a blood vessel) of the measurement part H. The blood quantity index M is expressed in Expression (1a) below. A sign $\langle I^2 \rangle$ in Expression (1a) is an average signal intensity over the whole bandwidth of the detection signal S or a signal intensity G(0) (that is, an intensity of a direct-current component) at 0 kHz in the intensity spectrum X.

$$M = \frac{\int_{f_L}^{f_H} G(f) df}{\langle I^2 \rangle} \quad (1a)$$

As understood from Expression (1a), the blood quantity index M is calculated by integrating the signal intensity G(f) of each frequency f in the intensity spectrum X in the frequency range N. The first index calculation unit 51 may calculate the blood quantity index M by calculating Expression (1b) below in which an integral of Expression (1a) is replaced with a total sum ($\Sigma$). The sign $\Delta f$ in Expression (1b) is a bandwidth corresponding to one signal intensity G(f) on the frequency axis and is equivalent to a horizontal width of each rectangle when the intensity spectrum X is approximated with a plurality of rectangles arranged on the frequency axis. The calculation of the blood quantity index M by the first index calculation unit 51 is repeatedly executed for each unit period.

$$M = \frac{\sum_{f=f_L}^{f_H} \Delta f \cdot G(f)}{\langle I^2 \rangle} \quad (1b)$$

The second index calculation unit 52 in FIG. 3 calculates blood flow index F (so-called FLOW value) from each frequency f within the frequency range N in the intensity spectrum X and the signal intensity G(f) of the signal component. The blood flow index F is an index of a blood flow of the measurement part H (that is, a volume of blood moving in an artery within the unit period). Specifically, the blood flow index F is expressed in Expression (2a) below.

$$F = \frac{\int_{f_L}^{f_H} f \cdot G(f) df}{\langle I^2 \rangle} \quad (2a)$$

As understood from Expression (2a), the blood flow index F is calculated by integrating a primary moment ($f \times G(f)$) which is a product of the signal intensity G(f) of each frequency f in the intensity spectrum X and the frequency f within the frequency range N. The second index calculation unit 52 may calculate the blood flow index F by calculating Expression (2b) below in which an integral of Expression (2a) is replaced with a total sum ($\Sigma$). The calculation of the blood flow index F by the second index calculation unit 52 is repeatedly executed for each unit period.

$$F = \frac{\sum_{f=f_L}^{f_H} f \cdot \Delta f \cdot G(f)}{\langle I^2 \rangle} \quad (2b)$$

The blood pressure calculation unit 44 in FIG. 3 calculates a blood pressure P of the measurement part H using the blood quantity index M and the blood flow index F calculated by the biological analysis unit 43. The calculation of the pressure P by the blood pressure calculation unit 44 is repeatedly executed for any period (for example, the beat period T). Specifically, the blood pressure calculation unit 44 calculates the blood pressure P of the beat period T from the blood quantity index M for each unit period of the beat period T and the blood flow index F for each unit period of the beat period T.

A relation among the blood quantity index M, the blood flow index F, and the blood pressure P will be described. The blood pressure P is expressed as a product of a blood flow Q and blood vessel resistance R (P=Q×R). The blood vessel resistance R is proportional to a reciprocal of a fourth power of a blood vessel diameter d (a sign a0 is a constant of proportionality), as expressed in Expression (3a) below. When it is assumed that the blood vessel diameter disproportional to a cubic root of the blood quantity index M and the blood flow Q is proportional to the blood flow index F, Expressions (3b) and (3c) below are established (signs a1 and a2 are constants of proportionality).

$$R = a_0 \cdot \frac{1}{d^4} \quad (3a)$$

$$d = a_1 \cdot M^{1/3} \quad (3b)$$

$$Q = a_2 \cdot F \quad (3c)$$

In consideration of the above-described relations, Expression (4) below expressing a relation among the blood quantity index M, the blood flow index F, and the blood pressure P is derived.

$$P = a_0 \frac{Q}{d^4} = \frac{a_0 \cdot a_2 \cdot F}{(a_1 \cdot M^{1/3})^4} = a \cdot \frac{F}{M^{4/3}} \quad (4)$$

$$(a = a_0 \cdot a_2 / a_1^4)$$

The blood pressure calculation unit 44 calculates the blood pressure P of the measurement part H by calculating Expression (4) using the blood quantity index M calculated by the first index calculation unit 51 and the blood flow index F calculated by the second index calculation unit 52. As described above, since the calculation of the blood pressure P by the blood pressure calculation unit 44 is repeatedly executed for each unit period, a temporal change in the blood pressure P (a time series of the blood pressure P) of the measurement part H is measured. The control device 21 causes the display device 23 to display the blood pressure P calculated by the blood pressure calculation unit 44.

Setting of Frequency Range N

The setting of the frequency range N by the range setting unit 42 will be described in detail. Here, to calculate the blood pressure P with high precision, it is necessary to specify appropriate biological indexes (the blood quantity index M and the blood flow index F) in which a beat of a biological body is reflected. Accordingly, the range setting unit 42 according to the first embodiment sets the frequency range N in which a beat of a biological body is appropriately reflected in the intensity spectrum X.

Figure 5:
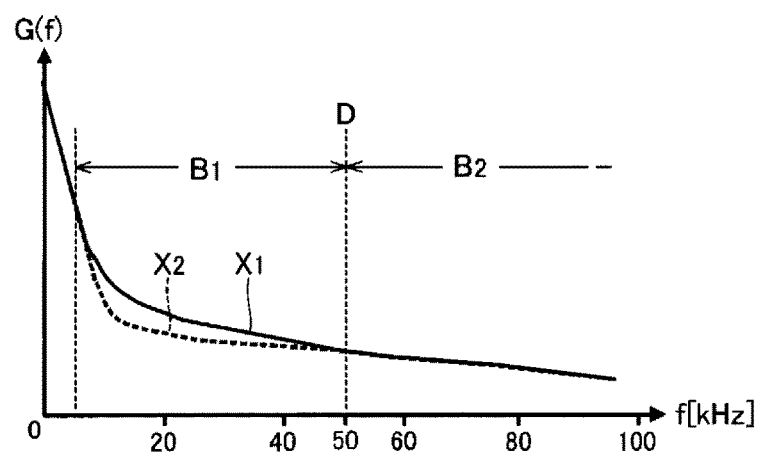
FIG. 5 is a graph illustrating a first intensity spectrum and a second intensity spectrum.

FIG. 5 is a graph illustrating the intensity spectrum X at a first time point at which a heart is most contracted during the beat period T (hereinafter referred to as a "first intensity spectrum X1") and the intensity spectrum X at a second time point at which a heart is most expanded during the beat period T (hereinafter referred to as a "second intensity spectrum X2"). The first time point is a time point at which the blood quantity index M or the blood flow index F is maximum within the beat period T and the second time point is a time point at which the blood quantity index M or the blood flow index F is minimum within the beat period T.

FIG. 5 illustrates a bandwidth in which a temporal change in the signal intensity G(f) is large (hereinafter referred to as a "first bandwidth") B1 and a bandwidth in which the temporal change in the signal intensity G(f) is less than that of the first bandwidth B1 (hereinafter referred to as a "second bandwidth") B2 in the first intensity spectrum X1 and the second intensity spectrum X2. The second bandwidth B2 is located closer to a high frequency side than the first bandwidth B1. The first bandwidth B1 and the second bandwidth B2 continue. A component of the first bandwidth B1 in the intensity spectrum X is a component in which an influence of a beat of a biological body is large (that is, interlocking with a beat). That is, a difference in the signal intensity G(f) at each frequency f in the first bandwidth B1 is large between the first intensity spectrum X1 and the second intensity spectrum X2. In contrast, a component of the second bandwidth B2 in the intensity spectrum X is a component in which an influence of a beat of a biological body is sufficiently small (that is, a change is small). That is, a difference in the signal intensity G(f) at each frequency f in the second bandwidth B2 is small between the first intensity spectrum X1 and the second intensity spectrum X2 (ideally, identical). As understood from the foregoing description, when the biological index is calculated from the signal intensity G(f) of the first bandwidth B1 in the intensity spectrum X, an appropriate biological index in which a beat of a biological body is reflected can be calculated. For the foregoing reason, the range setting unit 42 determines a frequency in a boundary between the first bandwidth B1 and the second bandwidth B2 (hereinafter simply referred to as a "boundary") D as the upper limit fH of the frequency range N.

The range setting unit 42 in FIG. 3 includes a change calculation unit 61 and a boundary determination unit 62. The change calculation unit 61 calculates an index of a temporal change quantity of the signal intensity G(f) for each frequency (hereinafter referred to as a "change index") V(f) in the plurality of intensity spectra X. In the first embodiment, the frequency analysis unit 41 calculates the change index V(f) for each frequency in the first intensity spectrum X1 and the second intensity spectrum X2 among the plurality of intensity spectra X calculated during the beat period T by the frequency analysis unit 41. Specifically, the change calculation unit 61 calculates the change index V(f) in accordance with a difference in the signal intensity G(f) between the first intensity spectrum X1 and the second intensity spectrum X2. The change calculation unit 61 according to the first embodiment calculates the change index V(f) by dividing the difference (generally, the absolute value of the difference) in the signal intensity G(f) between the first intensity spectrum X1 and the second intensity spectrum X2 by an average Gave of the signal intensity G(f) between the first intensity spectrum X1 and the second intensity spectrum X2. Specifically, the change index V(f) is expressed in Expression (5) below. A sign G1($f$) denotes a signal intensity of the first intensity spectrum X1 at any one frequency f and a sign G2($f$) denotes a signal intensity of the second intensity spectrum X2 at the frequency f.

$$V(f) = \frac{|G1(f) - G2(f)|}{G_{ave}} \quad (5)$$

Figure 6:
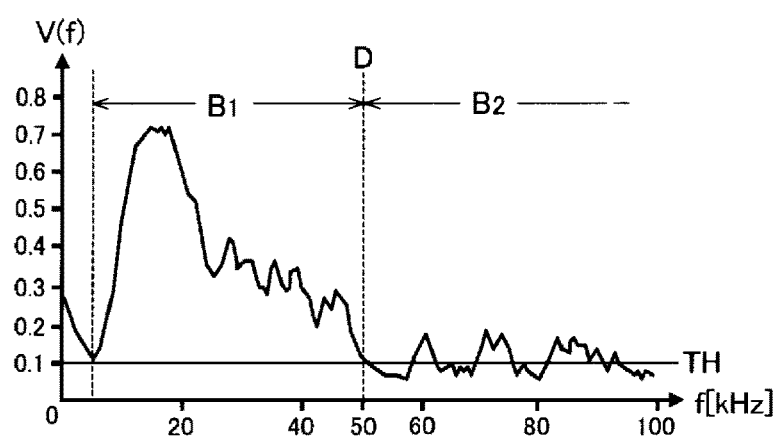
FIG. 6 is a graph illustrating a change index.

FIG. 6 is a graph illustrating the change index V(f) for each frequency f in the first intensity spectrum X1 and the second intensity spectrum X2. FIG. 6 illustrates a graph after the change index V(f) for each frequency f is smoothed. As a difference (G1($f$)–G2($f$)) in the signal intensity between the first intensity spectrum X1 and the second intensity spectrum X2 is larger, the change index V(f) is larger. That is, in general, there is a tendency that the change index V(f) calculated in the first bandwidth B1 between the first intensity spectrum X1 and the second intensity spectrum X2 is greater than the change index V(f) calculated in the second bandwidth B2. Specifically, an average value of the change index V(f) in the first bandwidth B1 is greater than an average value of the change index V(f) in the second bandwidth B2.

The boundary determination unit 62 in FIG. 3 determines a boundary D between the first bandwidth B1 and the second bandwidth B2 in the first intensity spectrum X1 and the second intensity spectrum X2. Specifically, the boundary determination unit 62 determines the boundary D in accordance with the change index V(f) calculated by the change calculation unit 61. As exemplified in FIG. 6, for example, the frequency f at which the change index V(f) is less than a predetermined threshold TH is determined as the boundary D. As described above, the signal intensities for each frequency f in the second bandwidth B2 are ideally identical in the first intensity spectrum X1 and the second intensity spectrum X2. Accordingly, the change index V(f) calculated by calculating Expression (5) in the second bandwidth B2 is substantially constant throughout the second bandwidth B2 at a value less than the change index V(f) of the first bandwidth B1. In consideration of the foregoing circumstances, in the first embodiment, an average value of the change index V(f) in a frequency bandwidth sufficiently greater than the assumed boundary D (that is, a frequency bandwidth assumed to be the second bandwidth B2) is set in advance as the threshold TH. For example, an average value of the change index V(f) in a frequency bandwidth of 80 kHz to 100 kHz is appropriate as the threshold value TH. FIG. 6 illustrates a case in which the threshold TH is set to 0.1. The boundary determination unit 62 according to the first embodiment determines a minimum frequency (50 kHz in the example of FIG. 6) among frequencies at which the change index V(f) is less than the threshold TH as the boundary D. That is, when the change index V(f) is observed from a low frequency side to a high frequency side on the frequency axis, the frequency f first reduced from a numerical value greater than the threshold TH to a numerical value less than the threshold TH is specified as the boundary D. The boundary determination unit 62 sets the determined boundary D as an upper limit fH of the frequency range N. A lower limit fL of the frequency range N is set to a numerical value (for example, 0.1 kHz) equal to or greater than 0 kHz.

Figure 7:
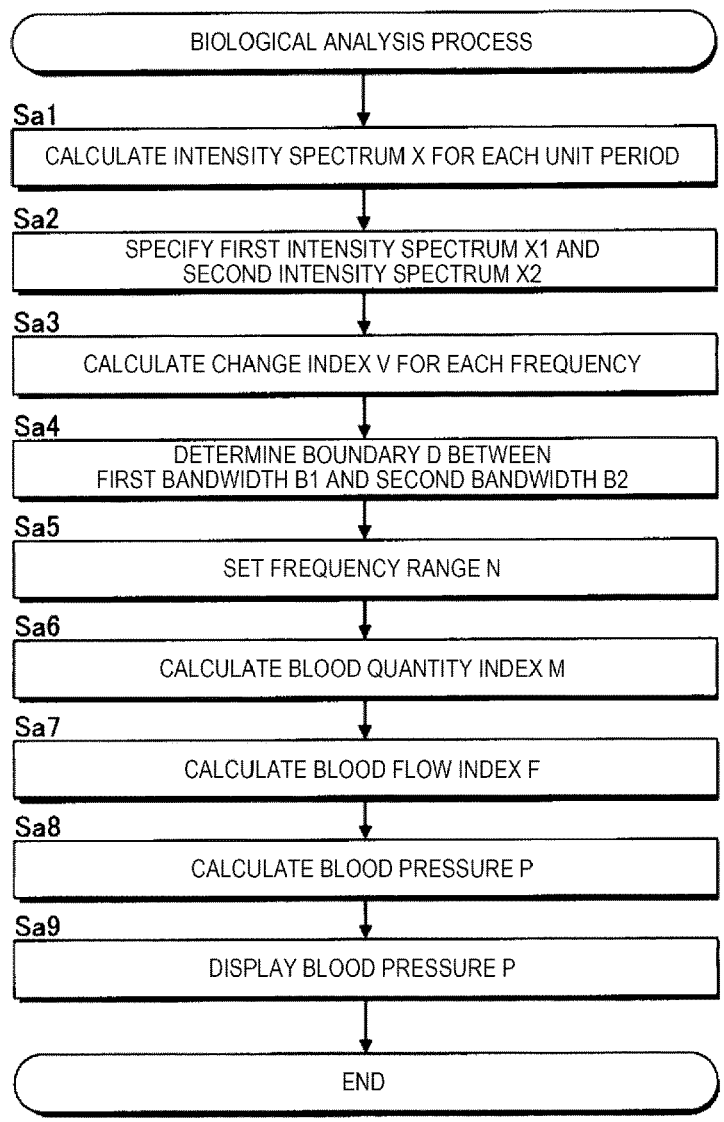
FIG. 7 is a flowchart illustrating a biological analysis process executed by the control device.

FIG. 7 is a flowchart illustrating a process (hereinafter referred to as a "biological analysis process") executed by the control device 21. For example, using an instruction from a user as a trigger, the biological analysis process of FIG. 7 is executed along with generation of the detection signal S by the detection device 30. When the biological analysis process starts, the frequency analysis unit 41 calculates the intensity spectrum X for each unit period from the detection signal S (Sa1). That is, the plurality of intensity spectra X within the unit period are sequentially calculated. The change calculation unit 61 specifies the first intensity spectrum X1 and the second intensity spectrum X2 from the plurality of calculated intensity spectra X (Sa2). A method of specifying the first intensity spectrum X1 and the second intensity spectrum X2 is as follows.

Figure 8:
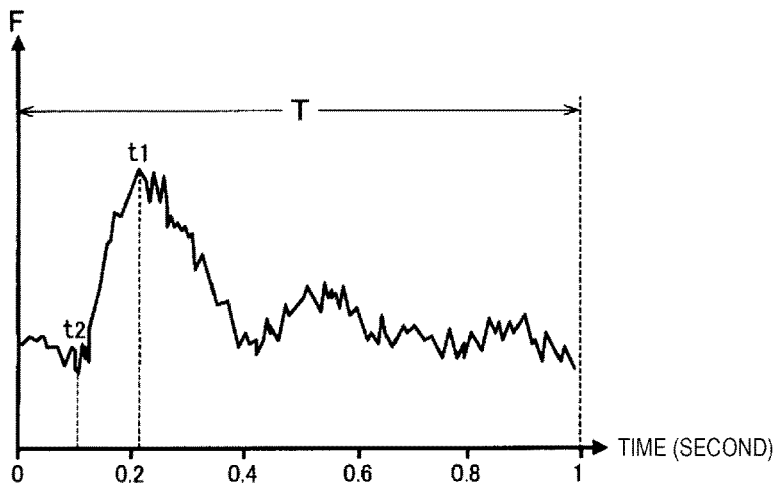
FIG. 8 is a graph illustrating a temporal change in a blood flow index.

First, the change calculation unit 61 calculates the blood flow index F of the intensity spectrum X by calculating Expression (2a) or (2b) in which a provisional frequency range N is applied to each of the plurality of intensity spectra X. The provisional frequency range N is a frequency bandwidth in which the lower limit fL and the upper limit fH are set to predetermined values (for example, values irrespective of a state of a biological body). FIG. 8 is a graph illustrating a temporal change in the blood flow index F. As illustrated in FIG. 8, the change calculation unit 61 demarcates the beat period T from a time series of the plurality of blood flow indexes F. FIG. 8 illustrates a case in which the beat period T is demarcated to 1 second. Subsequently, the change calculation unit 61 specifies the intensity spectrum X at a first time point t1 at which the blood flow index F is maximum during the beat period T as the first intensity spectrum X1 and specifies the intensity spectrum X at a second time point t2 at which the blood flow index F is minimum during the beat period T as the second intensity spectrum X2. Here, the blood flow index F has been focused on, but the beat period T, the first time point t1, and the second time point t2 may be specified from the temporal change in the blood quantity index M.

The change calculation unit 61 calculates the change index V(f) in the first intensity spectrum X1 and the second intensity spectrum X2 (Sa3). Specifically, the change index V(f) is calculated in accordance with a difference in the signal intensity between the first intensity spectrum X1 and the second intensity spectrum X2. In the calculation of the change index V(f), Expression (5) described above is used.

The boundary determination unit 62 determines the boundary D between the first bandwidth B1 and the second bandwidth B2 in the first intensity spectrum X1 and the second intensity spectrum X2 in accordance with the change index V(f) (Sa4). Subsequently, the boundary determination unit 62 sets the frequency range N in which a value (for example, 0.1 kHz) greater than 0 kHz is the lower limit fL and the boundary D is the upper limit fH (Sa5). The frequency range N is set for each beat period T.

The first index calculation unit 51 calculates the blood quantity index M from the signal intensity G(f) within the frequency range N in the intensity spectrum X (Sa6). In the calculation of the blood quantity index M, Expression (1a) or (1b) described above is used. The second index calculation unit 52 calculates the blood flow index F from the signal intensity G(f) within the frequency range N in the intensity spectrum X (Sa7). In the calculation of the blood flow index F, Expression (2a) or (2b) described above is used. The processes from step Sa6 to step Sa7 are executed for each unit period. Then, the blood pressure calculation unit 44 calculates the pressure P of the measurement part H using the blood quantity index M calculated by the first index calculation unit 51 and the blood flow index F calculated by the second index calculation unit 52 (Sa8). The process of step Sa8 is executed for each arbitrary period (for example, each beat period T). In steps Sa6 and Sa7, the frequency range N set in the beat period T is commonly used in the plurality of intensity spectra X calculated within the one arbitrary beat period T. The control device 21 causes the display device 23 to display the blood pressure P calculated by the blood pressure calculation unit 44 (Sa9).

As understood from the foregoing description, in the first embodiment, the biological index (the blood quantity index M or the blood flow index F) is calculated from the signal intensity within the frequency range N in which the boundary D between the first bandwidth B1 and the second bandwidth B2 is the upper limit fH in the plurality of sequentially calculated intensity spectra X of light reflected and received inside a biological body through radiation of a laser beam. Accordingly, compared to a configuration in which the biological index is calculated from an intensity within the frequency range N in which a portion (for example, a frequency in the second bandwidth B2) other than the boundary D between the first bandwidth B1 and the second bandwidth B2 is the upper limit fH, it is possible to calculate the appropriate biological index in which a beat of the biological body is reflected.

In the first embodiment, in particular, the change index V(f) is calculated in accordance with the difference in the signal intensity between the first intensity spectrum X1 and the second intensity spectrum X2. Therefore, compared to a configuration in which the change index V(f) is calculated in accordance with the difference in the signal intensity between the two intensity spectra X at two time points selected irrespective of magnitude of the detection signal S, it is possible to calculate the change index V(f) in which the difference in the signal intensity between the two intensity spectra X is appropriately reflected.

Second Embodiment

A second embodiment of the invention will be described. Elements similar to those of the first embodiment in operations or functions in each embodiment to be exemplified below, the reference numerals used in the description of the first embodiment are applied, and a detailed description of each element will be appropriately omitted.

The change calculation unit 61 according to the first embodiment has calculated the change index V(f) in accordance with the difference in the signal intensity between the first intensity spectrum X1 and the second intensity spectrum X2 among the plurality of intensity spectra X within the beat period T. In the second embodiment, however, the change calculation unit 61 calculates the change index V(f) in accordance with the degree of scattering of the signal intensity for each frequency in the plurality of intensity spectra X within the beat period T. Specifically, the change calculation unit 61 calculates the change index V(f) by dividing a standard deviation σ(f) of the signal intensity for each frequency in the plurality of intensity spectra X by an average Gave of the signal intensities between the plurality of intensity spectra X. The change index V(f) according to the second embodiment is expressed in Expression (6) below instead of Expression (5) described above. The sign σ(f) denotes a standard deviation (the state of dispersion of the signal intensity) of the signal intensity G(f) at any frequency f in the plurality of intensity spectra X.

$$V(f) = \frac{|\sigma(f)|}{G_{ave}} \quad (6)$$

Figure 9:
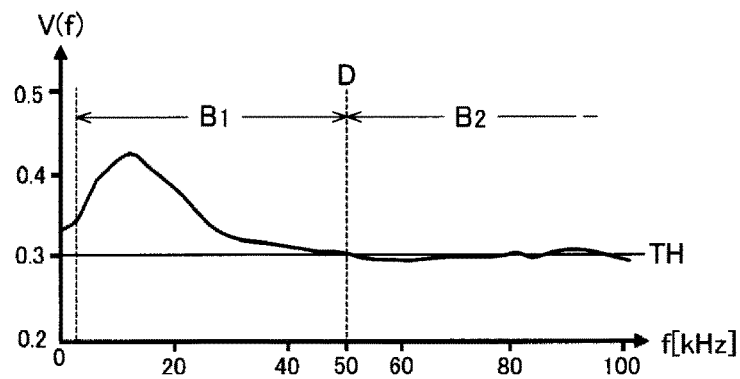
FIG. 9 is a graph illustrating a change index according to a second embodiment.

FIG. 9 is a graph illustrating the change index V(f) for each frequency in the plurality of intensity spectra X. The change index V(f) is larger as the standard deviation of the signal intensity in the plurality of intensity spectra X is larger (that is, a variation is larger). As described above, the temporal change in a component of the first bandwidth B1 in the intensity spectrum X is large and a temporal change in a component of the second bandwidth B2 in the intensity spectrum X is small (ideally, there is no change). Accordingly, it is possible to obtain a tendency that the change index V(f) calculated in the first bandwidth B1 in the plurality of intensity spectra X is greater than the change index V(f) calculated in the second bandwidth B2.

The boundary determination unit 62 according to the second embodiment determines the boundary D between the first bandwidth B1 and the second bandwidth B2 in the plurality of intensity spectra X within the beat period T. As in the first embodiment, a frequency at which the change index V(f) in FIG. 9 is less than the predetermined threshold TH is determined as the boundary D. Since the signal intensity at each frequency f in the second bandwidth B2 is ideally identical, the change index V(f) calculated by calculating Expression (6) in the second bandwidth B2 is substantially constant at a value less than the change index V(f) of the first bandwidth B1 throughout the second bandwidth B2. Accordingly, as in the first embodiment, an average value of the change index V(f) in a frequency bandwidth (for example, 80 kHz to 100 kHz) sufficiently greater than the assumed boundary D is set in advance as the threshold TH. FIG. 9 illustrates a case in which the threshold TH is set to 0.3. The boundary determination unit 62 according to the second embodiment determines a minimum frequency (50 kHz in the example of FIG. 9) among the frequencies at which the change index V(f) is less than the threshold TH as the boundary D as in the first embodiment. The boundary determination unit 62 sets the determined boundary D as the upper limit fH of the frequency range N. In the second embodiment, step Sa2 (a process of specifying the first intensity spectrum X1 and the second intensity spectrum X2) of the flowchart of FIG. 7 is omitted.

In the second embodiment, the biological index is calculated from the signal intensity within the frequency range N in which the boundary D between the first bandwidth B1 and the second bandwidth B2 in the plurality of intensity spectra X is the upper limit fH as in the first embodiment. Therefore, it is possible to calculate the appropriate biological index in which a beat of the biological body is reflected. In the second embodiment, it is possible to calculate the appropriate change index V(f) in accordance with the degree of scattering of the signal intensity in the plurality of intensity spectra X.

Third Embodiment

Figure 10:
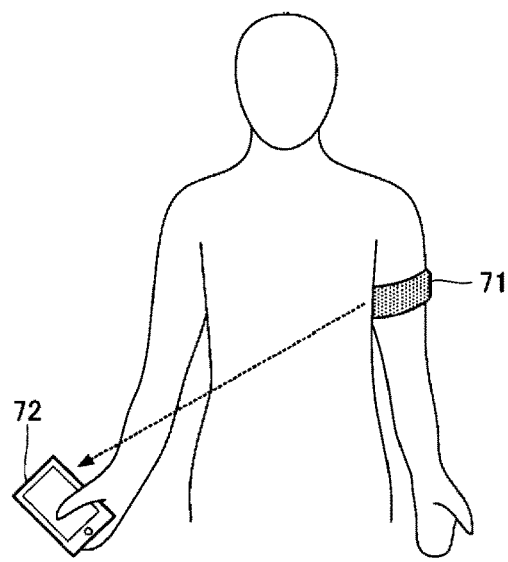
FIG. 10 is a schematic diagram illustrating a use example of a biological analysis device according to a third embodiment.
Figure 11:
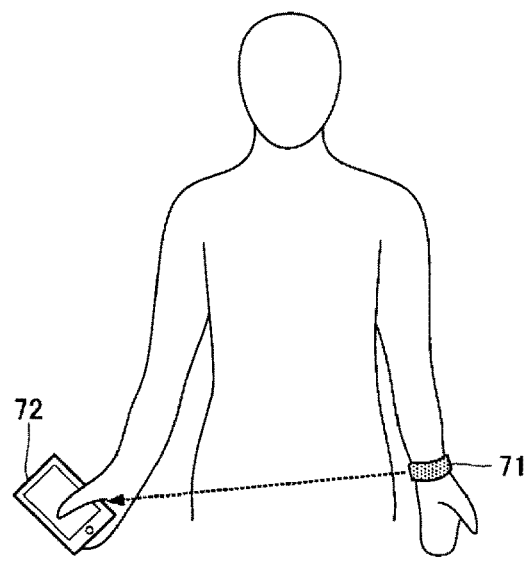
FIG. 11 is a schematic diagram illustrating another use example of the biological analysis device according to the third embodiment.

FIG. 10 is a schematic diagram illustrating a use example of a biological analysis device 100 according to a third embodiment. As exemplified in FIG. 10, the biological analysis device 100 includes a detection unit 71 and a display unit 72 configured to be separate from each other. The detection unit 71 includes the detection device 30 exemplified in each of the above-described embodiment. In FIG. 10, the detection unit 71 worn on an upper arm of a subject is exemplified. As exemplified in FIG. 11, the detection unit 71 worn on a wrist of a subject is also appropriate.

The display unit 72 includes the display device 23 exemplified in each of the above-described embodiments. For example, an information terminal such as a mobile phone or a smartphone is an appropriate example of the display unit 72. Here, any specific form of the display unit 72 is used. For example, a wrist watch type information terminal which can be carried by the subject or an information terminal dedicated for the biological analysis device 100 may be used as the display unit 72.

An element (hereinafter referred to as a "calculation processing unit") calculating the indexes (the blood quantity index M, the blood flow index F, and the blood pressure P) from the detection signal S is mounted on the display unit 72, for example. The calculation processing unit includes the elements exemplified in FIG. 3 (the frequency analysis unit 41, the range setting unit 42, the biological analysis unit 43, and the blood pressure calculation unit 44). The detection signal S generated by the detection device 30 of the detection unit 71 is transmitted to the display unit 72 in a wired or wireless manner. The calculation processing unit of the display unit 72 calculates the biological indexes (the blood quantity index M and the blood flow index F) and the blood pressure P from the detection signal S and displays the biological indexes (the blood quantity index M and the blood flow index F) and the blood pressure P on the display device 23.

The calculation processing unit may be mounted on the detection unit 71. The calculation processing unit calculates the biological indexes and the blood pressure P from the detection signal S generated by the detection device 30 and transmits data for displaying the biological indexes to the display unit 72 in a wired or wireless manner. The display device 23 of the display unit 72 displays the biological indexes indicated by the data received from the detection unit 71.

Supplement of Upper Limit fH

As has been exemplified in each of the above-described embodiments, according to a preferred aspect of the invention, a configuration in which the boundary D between the first bandwidth B1 and the second bandwidth B2 in the plurality of intensity spectra X is set as the upper limit fH of the frequency range N (hereinafter referred to as a "configuration A") is adopted. An action which can be observed from an actual biological analysis device (hereinafter referred to as an "actual product") by adopting the configuration A will be described below.

First, a method of estimating a range (frequency bandwidth) including the upper limit fH of the frequency range N in the configuration of the actual product calculating and displaying a blood flow index F(n) using the frequency range N of an intensity spectrum X(n) will be described.

Figure 12:
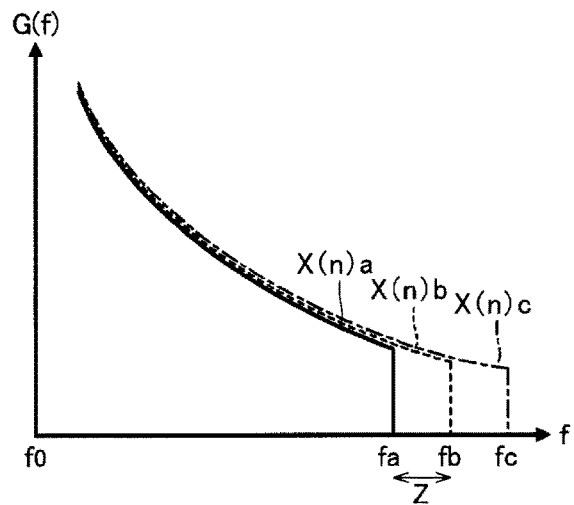
FIG. 12 is a graph illustrating a representative intensity spectrum related to supplement of an upper limit of a frequency range.

A scene in which a plurality of input signals I(n) are supplied from an external device to a wiring or a terminal to which the detection signal S is supplied in the actual product is assumed. FIG. 12 is a graph illustrating the intensity spectrum X(n) of a representative input signal I(n). FIG. 12 illustrates three cases in which the signal intensity G(f) equal to or greater than a specific frequency is 0 in any one intensity spectrum X(n). In an intensity spectrum X(n) a, a signal intensity equal to or greater than a frequency fa is 0. In an intensity spectrum X(n)b, a signal intensity equal to or greater than a frequency fb (>fa) is 0. In an intensity spectrum X(n)c, a signal intensity equal to or greater than a frequency fc (>fb) is 0. In FIG. 12, a portion overlapping in each intensity spectrum X (for example, a frequency bandwidth from f0 to fa) is actually identical although is shifted for convenience. By executing inverse Fourier transform on each intensity spectrum X, an input signal I(n) corresponding to the intensity spectrum X(n) is generated. Specifically, an input signal I(n)a corresponding to the intensity spectrum X(n)a, an input signal I(n)b corresponding to the intensity spectrum X(n)b, and an input signal I(n)c corresponding to the intensity spectrum X(n)c are generated.

A case in which the blood flow index F is displayed as a measurement result of a blood flow of a subject on the actual product is assumed. When the input signal I(n)a is supplied to the actual product, a blood flow index F(n)a is displayed. When the input signal I(n)b is supplied to the actual product, a blood flow index F(n)b is displayed. When the input signal I(n)c is supplied to the actual product, a blood flow index F(n)c is displayed. When the blood flow index F(n)b is greater than the blood flow index F(n)a (hereinafter referred to as "Condition 1") and the blood flow index F(n)b and the blood flow index F(n)c are identical (hereinafter referred to as "Condition 2"), the upper limit fH of the frequency range N used in the calculation of the blood flow index F in the intensity spectrum X(n) can be said to be greater than the frequency fa and equal to or less than the frequency fb (where fa<fH≤fb). This is because when the upper limit fH of the frequency range N is less than a frequency a, the blood flow index F(n)a and the blood flow index F(n)b are identical, and when the upper limit fH is greater than a frequency b, the blood flow index F(n)b and the blood flow index F(n)c are different. As understood from the foregoing description, by setting the frequency fa, the frequency fb, and the frequency fc so that both of Condition 1 and Condition 2 are satisfied, it is possible to estimate that the upper limit fH of the frequency range N is within a range Z between the frequency fa and the frequency fb.

Figure 13:
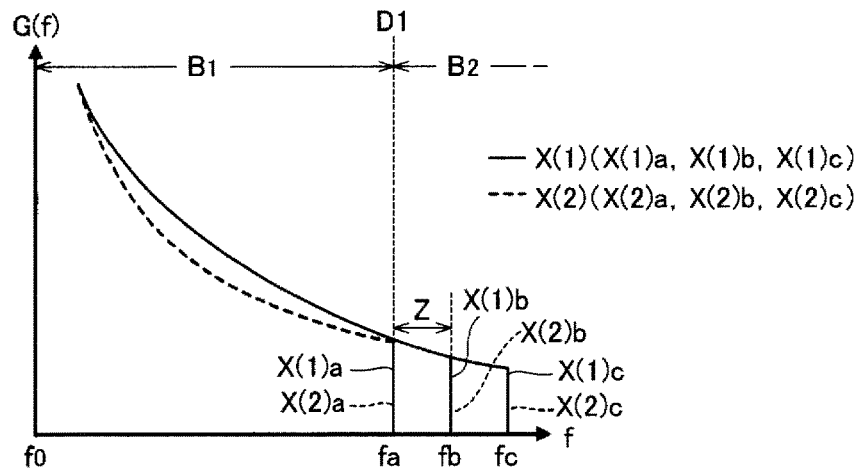
FIG. 13 is a graph illustrating an intensity spectrum related to supplement of an upper limit of a frequency.

FIG. 13 illustrates three kinds of intensity spectra X(1) (X(1)a to X(1)c) (indicated by a solid line) and three kinds of intensity spectra X(2) (X(2)a to X(2)c) (indicated by a dotted line). In each of the three kinds of intensity spectra X(1) (X(1)a to X(1)c), the signal intensity is 0 in a range equal to or greater than the specific frequencies fa to fc. Similarly, in each of the three kinds of intensity spectra X(2) (X(2)a to X(2)c), the signal intensity is 0 in a range equal to or greater than the specific frequencies fa to fc. As exemplified in FIG. 13, in the intensity spectrum X(1) and the intensity spectrum X(2), the signal intensity is different in the frequency bandwidth from the frequency f0 to the frequency fa. However, the signal intensity is identical in the frequency bandwidth equal to or greater than the frequency fa. That is, in the intensity spectrum X1 and the intensity spectrum X2, the frequency bandwidth from the frequency f0 to the frequency fa is the first bandwidth B1 and the frequency bandwidth equal to or greater than the frequency fa is the second bandwidth B2. That is, a boundary D1 between the first bandwidth B1 and the second bandwidth B2 is the frequency fa.

As described with reference to FIG. 12, when Condition 1 and Condition 2 are established in the intensity spectrum X1 and the intensity spectrum X2 in FIG. 13, it can be said that the upper limit fH of the frequency range N is located in the range Z greater than the frequency fa and equal to or less than the frequency fb.

Figure 14:
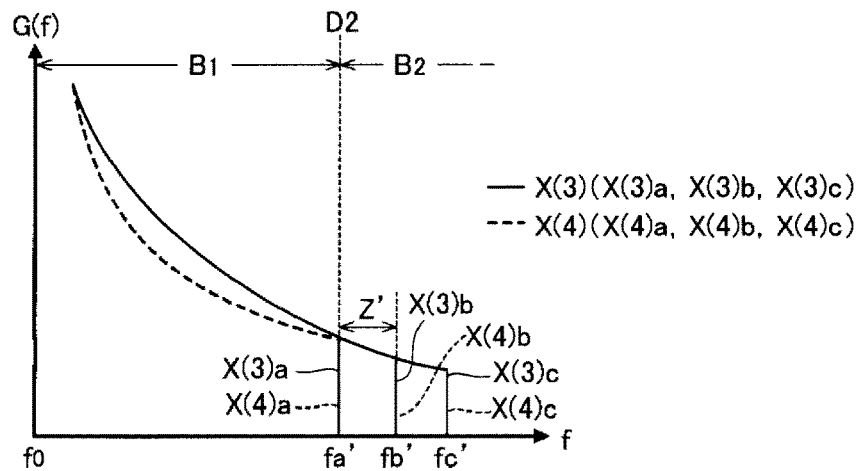
FIG. 14 is a graph illustrating another intensity spectrum related to supplement of an upper limit of a frequency.

On the other hand, FIG. 14 illustrates three kinds of intensity spectra X(3) (X(3)a to X(3)c) and three kinds of intensity spectra X(4) (X(4)a to X(4)c) generated so that a frequency fa' less than the boundary D1 in FIG. 13 is a boundary D2 between the first bandwidth B1 and the second bandwidth B2. In each of the three kinds of intensity spectra X(3)a to X(3)c, the signal intensity is 0 in a range equal to or greater than specific frequencies fa' to fc'. Similarly, in each of the three kinds of intensity spectra X(4)a to X(4)c, the signal intensity is 0 in the range equal to or greater than the specific frequencies fa' to fc'. As exemplified in FIG. 14, in the intensity spectrum X(3) and the intensity spectrum X(4), the signal intensity is different in the frequency bandwidth from the frequency f0 to the frequency fa'. However, the signal intensity is identical in the frequency bandwidth equal to or greater than the frequency fa'. FIG. 14 exemplifies the case in which the frequency fa' less than the boundary D1 is the boundary D2, but a frequency greater than the boundary D1 may be the boundary D2. That is, the frequencies of the boundary D1 and the boundary D2 may be different.

As described with reference to FIG. 12, when Condition 1 and Condition 2 are established in the intensity spectrum X(3) and the intensity spectrum X(4) in FIG. 14, it can be said that the upper limit fH of the frequency range N is located in a range Z' greater than the frequency fa' and equal to or less than the frequency fb'.

When the range Z in FIG. 13 and the range Z' in FIG. 14 are different on the frequency axis (for example, the range Z and the range Z' do not overlap), it can be said that the upper limit fH of the frequency range N is changed in accordance with the position (frequency) of the boundary D. That is, the configuration A can be determined to be adopted in the actual product. On the other hand, when the range Z in FIG. 13 and the range Z' in FIG. 14 overlap on the frequency axis, it can be said that the upper limit fH of the frequency range N does not depend on the position of the boundary D.

In the foregoing description, the blood flow index F has been focused on. The biological index for determining whether the configuration A is adopted in the actual product is not limited to the foregoing example. For example, the blood quantity index M can also be used.

Modification Examples

Each of the embodiments exemplified above can be modified in various forms. Specific modification aspects will be exemplified below. Two or more selected arbitrarily from the following examples can also be merged appropriately.

(1) In each of the above-described embodiments, the configuration in which the biological analysis device 100 includes the blood pressure calculation unit 44 has been exemplified, but the blood pressure calculation unit 44 may be omitted from the biological analysis device. For example, the display device 23 displays one or both of the blood quantity index M calculated by the first index calculation unit 51 and the blood flow index F calculated by the second index calculation unit 52. The biological analysis device 100 calculating the blood quantity index M may be a blood quantity meter and the biological analysis device calculating the blood flow index F may be a blood flow meter. One of the first index calculation unit 51 and the second index calculation unit 52 and the blood pressure calculation unit 44 may be omitted and one of the blood quantity index M and the blood flow index F may be displayed on the display device 23. According to each of the above-described embodiments in which the blood pressure calculation unit 44 is included, there is the advantage that a blood pressure which is a basic and important index for diagnosing a state of a biological body can be calculated.

(2) In each of the above-described embodiments, the blood quantity index M and the blood flow index F have been exemplified as the biological indexes, but the kinds of biological indexes are not limited to the foregoing examples. For example, a blood vessel diameter or the cross-sectional area of a blood vessel in accordance with the blood quantity index M, a blood flow in accordance with the blood flow index F, or a blood flow rate obtained by dividing a blood flow by the cross-sectional area of a blood vessel can also be calculated as a biological index by the biological analysis unit 43. A vascular age (an index of vascular hardness) may be calculated from the above-exemplified biological indexes and a subject may be informed of the vascular age. A state of a blood flow of a subject from the above-described biological index can also be specified from a plurality of stages (for example, abnormality/high side/normality and the like) and a subject can be informed of the state of the blood flow.

In each of the above-described embodiments, the blood pressure calculation unit 44 has calculated the blood pressure P, but the index calculated by the blood pressure calculation unit 44 is not limited to the blood pressure P. For example, an average blood pressure and a pulse pressure can also be calculated by the blood pressure calculation unit 44. As understood from the foregoing description, the index calculated by the blood pressure calculation unit 44 is expressed comprehensively as an index related to the blood pressure P of a biological body (hereinafter referred to as a "blood pressure index"). A state of a blood pressure of a subject from the above-described biological index can also be specified from a plurality of stages (for example, abnormality/high side/normality and the like) and a subject can be informed of the state of the blood pressure.

(3) In each of the above-described embodiments, the boundary D between the first bandwidth B1 and the second bandwidth B2 has been determined in accordance with the change index V(f), but a method of determining the boundary D is not limited to the foregoing example. For example, when a time series of the plurality of intensity spectra X is displayed on the display device 23, a user operates the operation device 24 to give an instruction of the boundary D while confirming the display. The boundary determination unit 62 sets the boundary D in response to the instruction on the operation device 24 by the user. That is, the change calculation unit 61 may not be provided. Here, according to each of the above-described embodiments in which the boundary D between the first bandwidth B1 and the second bandwidth B2 is determined in accordance with the change index V(f), it is possible to appropriately determine the boundary D between the first bandwidth B1 and the second bandwidth B2 in accordance with the change index V(f).

(4) In the first embodiment, the first intensity spectrum X1 and the second intensity spectrum X2 among the plurality of intensity spectra X have been specified in accordance with the blood quantity index M or the blood flow index F, but any index to be used to specify the first intensity spectrum X1 and the second intensity spectrum X2 can be used as long as the index interlocks with a beat of a biological body (hereinafter referred to as a "beat index"). For example, a temporal change in the blood flow index F (or the blood quantity index M) may be smoothed and the first intensity spectrum X1 and the second intensity spectrum X2 may be specified from the smoothed temporal change. An integration value of each intensity spectrum X within the beat period T may be used. Specifically, among the plurality of intensity spectrum X within the beat period T, the intensity spectrum X in which the integration value is maximum is specified as the first intensity spectrum X1 and the intensity spectrum X in which the integration value is minimum is specified as the second intensity spectrum X2. In the configuration in which the integration value is used, it is not necessary to calculate the blood flow index F (or the blood quantity index M) in which the provisional frequency range N is used, to specify the first intensity spectrum X1 and the second intensity spectrum X2. Accordingly, a process of specifying the first intensity spectrum X1 and the second intensity spectrum X2 is simplified, and power saving of the device is expected. As another method, a pulse waveform (for example, a pressure pulse wave or a volume pulse wave) may be acquired, a time point at which a pulse is maximum (a time point at which a heart is most contracted) may be set as first time point t1, and a time point at which a pulse is minimum (a time point at which a heart is most expanded) may be set as a second time point t2.

As understood from the foregoing description, the intensity spectrum X at the first time point at which the beat index is maximum during the beat period T is specified as the first intensity spectrum X1, and the intensity spectrum X at the second time point at which the beat index is minimum is specified as the second intensity spectrum X2. The beat index is a concept that includes the integration value of the intensity spectrum X, the blood quantity index M or the blood flow index F, and the smoothed blood quantity index M or blood flow index F. The beat index is not limited to the foregoing example. For example, an index (for example, a blood vessel diameter) calculated from the blood quantity index M or an index (for example, a blood flow) calculated from the blood flow index F may be set as a beat index.

(5) In the first embodiment, the first intensity spectrum X1 and the second intensity spectrum X2 among the plurality of intensity spectra X have been used in the calculation of the change index V(f), but the intensity spectra X used in the calculation of the change index V(f) are not limited to the first intensity spectrum X1 and the second intensity spectrum X2. For example, two intensity spectra X at two time points selected irrespective of magnitude of the beat index may be used in the calculation of the change index V(f).

(6) In each of the above-described embodiments, the minimum frequency at which the change index V(f) is less than the threshold TH has been determined as the boundary D between the first bandwidth B1 and the second bandwidth B2, but the method of determining the boundary D is not limited to the foregoing example. For example, a site (frequency) at which the change index V(f) is continuously less than the threshold TH may be determined as the boundary D. The threshold TH may not necessarily be set to determine the boundary D. For example, a frequency between a bandwidth in which the change index V(f) is changed and a bandwidth in which the change index V(f) is substantially constant may be determined as the boundary D.

(7) In each of the above-described embodiments, the average value of the change index V(f) in the frequency bandwidth sufficiently greater than the assumed boundary D has been set as the threshold TH, but the set threshold TH is not limited to the foregoing example. For example, a value of the change index V(f) at a frequency between the bandwidth in which the change index V(f) is changed and the bandwidth in which the change index V(f) is substantially constant may be set as the threshold TH. A configuration in which a fixed value set in advance is used as the threshold TH or a configuration in which a variable value in accordance with an instruction from a user is used as the threshold TH is also assumed.

(8) In the first embodiment, the first intensity spectrum X1 and the second intensity spectrum X2 have been specified from the plurality of intensity spectra X within the beat period T. However, for example, the first intensity spectrum X1 and the second intensity spectrum X2 may be specified from the plurality of intensity spectra X within a period with a time length shorter than the beat period T. Here, in the configuration of the first embodiment in which the first intensity spectrum X1 and the second intensity spectrum X2 are specified from the plurality of intensity spectra X within the beat period T, the change index V(f) in which an influence of a beat of a biological body is appropriately reflected can be calculated, compared to a configuration in which the first intensity spectrum X and the second intensity spectrum X2 are specified from the plurality of intensity spectra X within a period shorter than 0.5 seconds.

In the second embodiment, the change index V(f) has been calculated in accordance with the degree of scattering of the signal intensity G(f) for each frequency in the plurality of intensity spectra X within the beat period T. However, the change index V(f) may be calculated in accordance with the degree of scattering of the signal intensity G(f) for each frequency in the plurality of intensity spectra X within a period longer than the beat period T.

(9) In the first embodiment, the change index V(f) has been calculated by dividing the difference in the signal intensity G(f) between the first intensity spectrum X1 and the second intensity spectrum X2 by the average Gave of the signal intensity G(f) between the first intensity spectrum X1 and the second intensity spectrum X2, but the method of calculating the change index V(f) is not limited to the foregoing example. For example, the change index V(f) may be calculated by dividing a ratio of the signal intensity G(f) between the first intensity spectrum X1 and the second intensity spectrum X2 by the average Gave.

The difference in the signal intensity G(f) between the first intensity spectrum X1 and the second intensity spectrum X2 may not necessarily be divided by the average Gave. Here, in the configuration of the first embodiment in which the change index V(f) is calculated by dividing the difference in the signal intensity G(f) between the first intensity spectrum X1 and the second intensity spectrum X2 by the average Gave, there is the advantage that it is possible to calculate the change index V(f) in which the temporal change in the signal intensity G(f) is more predominantly reflected, compared to a configuration in which the difference in the signal intensity G(f) between the first intensity spectrum X1 and the second intensity spectrum X2 is calculated as the change index V(f). That is, an influence of the tendency of the intensity spectrum X that the signal intensity G(f) attenuates on a high frequency side decreases. As understood from the foregoing description, any method of calculating the change index V(f) can be used as long as the change index V(f) is calculated in accordance with the difference in the signal intensity G(f) between the first intensity spectrum X1 and the second intensity spectrum X2.

(10) In the second embodiment, the change index V(f) has been calculated by dividing the standard deviation $\sigma(f)$ of the signal intensity G(f) for each frequency in the plurality of intensity spectra X by the average Gave of the signal intensity G(f) between the plurality of intensity spectra X, but the method of calculating the change index V(f) is not limited to the foregoing example. For example, the change index V(f) may be calculated by dividing a dispersion $\sigma^2(f)$ of the signal intensity G(f) for each frequency in the plurality of intensity spectra X by the average Gave.

Dividing the standard deviation $\sigma(f)$ of the signal intensity G(f) for each frequency in the plurality of intensity spectra X by the average Gave may not be necessarily performed. In the configuration of the second embodiment in which the change index V(f) is calculated by dividing the standard deviation $\sigma(f)$ of the signal intensity G(f) for each frequency in the plurality of intensity spectra X by the average Gave, there is the advantage that it is possible to calculate the change index V(f) in which the temporal change in the signal intensity G(f) is more predominantly reflected, compared to a configuration in which the standard deviation $\sigma(f)$ of the signal intensity G(f) for each frequency in the plurality of intensity spectra X is calculated as a change index V(f). That is, an influence of the tendency of the intensity spectrum X that the signal intensity G(f) attenuates on a high frequency side decreases. As understood from the foregoing description, any method of calculating the change index V(f) can be used as long as the change index V(f) is calculated in accordance with the degree of scattering of the signal intensity G(f) for each frequency in the plurality of intensity spectra X.

In each of the above-described embodiments, the boundary D between the first bandwidth B1 and the second bandwidth B2 can also be determined in response to an instruction from a user on the operation device 24. For example, the user confirms the change index V(f) displayed on the display device 23 and inputs a frequency considered as the boundary D using the operation device 24. The boundary determination unit 62 sets the boundary D in accordance with the frequency input using the operation device 24.

(12) In each of the above-described embodiments, the biological analysis device 100 configured as a single device has been described, but as will be exemplified below, the plurality of components of the biological analysis device 100 can be realized as mutually separate devices. In the following description, an element calculating the indexes (the biological index and the blood pressure P) from the detection signal S is referred to as a "calculation processing unit 27". The calculation processing unit 27 includes, for example, the components exemplified in FIG. 3 (the frequency analysis unit 41, the range setting unit 42, the biological analysis unit 43, and the blood pressure calculation unit 44).

Figure 15:
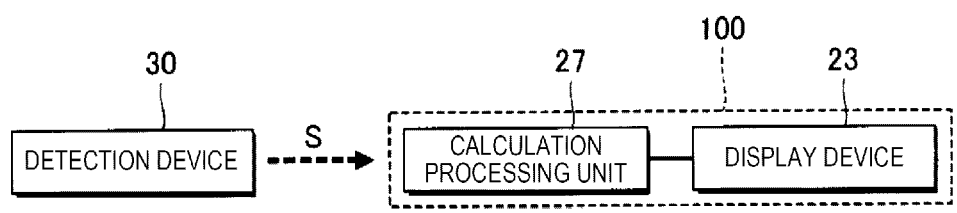
FIG. 15 is a diagram illustrating a configuration of a biological analysis device according to a modification example.

In each of the above-described embodiments, the biological analysis device 100 including the detection device 30 has been exemplified, but as exemplified in FIG. 15, the detection device 30 is assumed to be separate from the biological analysis device 100. The detection device 30 is, for example, a portable optical sensor module that is worn on the measurement part H such as a wrist, an upper arm, or the like of a subject. The biological analysis device 100 is realized as, for example, an information terminal such as a mobile phone or a smartphone. The biological analysis device 100 may be realized as a wrist watch type information terminal. The detection signal S generated by the detection device 30 is transmitted to the biological analysis device 100 in a wired or wireless manner. The calculation processing unit 27 of the biological analysis device 100 calculates the indexes (the blood quantity index M, the blood flow index F, and the blood pressure P) from the detection signal S and displays the indexes (the blood quantity index M, the blood flow index F, and the blood pressure P) on the display device 23. As understood from the foregoing description, the detection device 30 can be omitted from the biological analysis device 100.

Figure 16:
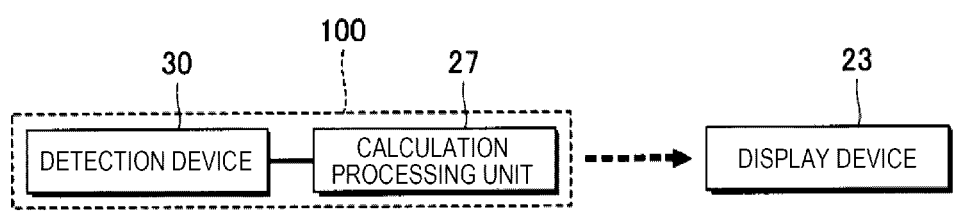
FIG. 16 is a diagram illustrating a configuration of a biological analysis device according to a modification example.

In each of the above-described embodiments, the biological analysis device 100 including the display device 23 has been exemplified, but as exemplified in FIG. 16, the display device 23 may be configured to be separate from the biological analysis device 100. The calculation processing unit 27 of the biological analysis device 100 calculates the indexes (the blood quantity index M, the blood flow index F, and the blood pressure P) from the detection signal S and transmits data for displaying the indexes to the display device 23. The display device 23 may be a dedicated display device, but may be mounted on, for example, an information terminal such as a mobile phone or a smartphone or a wrist watch type information terminal which can be carried by a subject. The indexes calculated by the calculation processing unit 27 of the biological analysis device 100 are transmitted to the display device 23 in a wired or wireless manner. The display device 23 displays the indexes received from the biological analysis device 100. As understood from the foregoing description, the display device 23 can be omitted from the biological analysis device 100.

Figure 17:
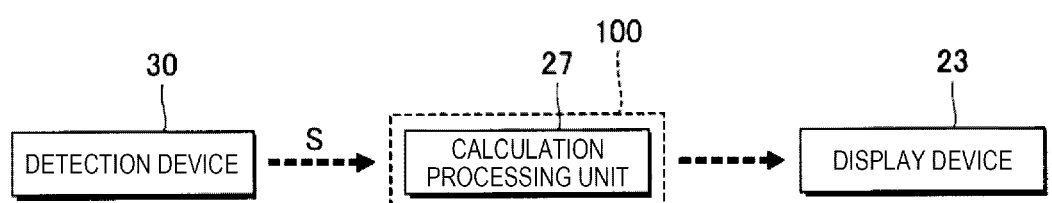
FIG. 17 is a diagram illustrating a configuration of a biological analysis device according to a modification example.

As exemplified in FIG. 17, the detection device 30 and the display device 23 are assumed to be separate from the biological analysis device 100 (the calculation processing unit 27). For example, the biological analysis device 100 (the calculation processing unit 27) is mounted on an information terminal such as a mobile phone or a smartphone.

In the configuration in which the detection device 30 is separate from the biological analysis device 100, the frequency analysis unit 41 can also be mounted on the detection device 30. The intensity spectrum X calculated by the frequency analysis unit 41 is transmitted from the detection device 30 to the biological analysis device 100 in a wired or wireless manner. As understood from the foregoing description, the frequency analysis unit 41 can be omitted from the biological analysis device 100.

(13) In each of the above-described embodiments, the wrist watch type biological analysis device 100 including the casing 12 and the belt 14 has been exemplified, but any specific form of the biological analysis device 100 can be used. For example, the biological analysis device of any type such as a patch type which can be attached to the body of a subject, an ear-mounted type which can be mounted on the ears of a subject, a finger-mounted type (for example, a nail-mounted type) which can be mounted on a finger of a subject, or a head-mounted type which can be mounted on the head of a subject can be adopted.

(14) In each of the above-described embodiments, the blood pressure P of a subject has been displayed on the display device 23, but the configuration in which the subject is informed of the blood pressure P is not limited to the foregoing example. For example, a subject can also be informed of the blood pressure P by sound. In the ear-mounted type biological analysis device which can be worn on the ears of a subject, a configuration in which the subject is informed of the blood pressure P by sound is particularly appropriate. The subject may not necessarily be informed of the blood pressure P. For example, the blood pressure P calculated by the biological analysis device 100 may be transmitted from a communication network to another communication device. The blood pressure P may be stored in the storage device 22 of the biological analysis device 100 or in a portable recording medium detachably mounted on the biological analysis device 100.

(15) The biological analysis device 100 according to each of the above-described embodiments is realized in cooperation with the control device 21 and a program, as exemplified above. The program according to a preferred aspect of the invention can be provided in a form stored in a recording medium which can be read by the computer to be installed on the computer. The program stored in a recording medium included in a delivery server can also be provided to a computer in a form delivered via a communication network. The recording medium is, for example, a non-transitory recording medium. An optical recording medium (optical disc) such as a CD-ROM is a good example, but a recording medium with any known format such as a semiconductor recording medium or a magnetic recording medium can be included. The non-transitory recording medium includes any recording medium removing a transitory and propagating signal, and a volatile recording medium is not excluded.

The entire disclosure of Japanese Patent Application No. 2017-202432, filed Oct. 19, 2017 is expressly incorporated by reference herein.

What is claimed is:

1. A biological analysis device comprising:
a CPU as a control device which:
determines a boundary between a first bandwidth in which a temporal change in a signal intensity is large and a second bandwidth which is located closer to a high frequency side than the first bandwidth and in which a temporal change in the signal intensity is less than the first bandwidth in a plurality of intensity spectra, within an intensity spectrum, related to frequencies calculated sequentially with regard to light reflected and received inside a biological body through radiation of a laser beam, uses the boundary to establish a frequency range in the intensity spectrum, the boundary being an upper limit of the frequency range, calculates a biological index related to a blood flow of the biological body from a signal intensity within the frequency range, and calculates a blood pressure P of the biological body according to Expression (4):

$$P = a_0 \frac{Q}{d^4} = \frac{a_0 \cdot a_2 \cdot F}{(a_1 \cdot M^{1/3})^4} = a \cdot \frac{F}{M^{4/3}} \quad (4)$$

$$(a = a_0 \cdot a_2 / a_1^4)$$

where P is the blood pressure, M is a blood quantity index obtained by integrating intensities in the intensity spectrum within the frequency range, F is a blood flow index obtained by integrating a product of an intensity of each frequency in the intensity spectrum and the frequency within the frequency range, a, $a_0$, $a_1$ and $a_2$ are constants, Q is a product of $a_0$, $a_2$ and F, and d is a product of a1 and $M^{1/3}$, wherein, in determining the boundary, the CPU:
calculates, sequentially, a change index which is an index of a temporal change quantity of the signal intensity for each frequency in the plurality of intensity spectra,
determines whether the change index at a frequency is less than a predetermined threshold, and
determines the frequency at which the change index is less than the predetermined threshold as the boundary.

2. The biological analysis device according to claim 1, wherein the CPU calculates the change index in accordance with a difference in a signal intensity between an intensity spectrum at a first time point at which a beat index interlocking with a beat of the biological body is maximum within a predetermined period and an intensity spectrum at a second time point at which the beat index interlocking with the beat of the biological body is minimum within the predetermined period among the plurality of intensity spectra.

3. The biological analysis device according to claim 2, wherein the predetermined period is equal to or greater than 0.5 seconds and equal to or less than 2 seconds.

4. The biological analysis device according to claim 2, wherein the CPU calculates the change index by dividing the difference in the signal intensity between the intensity spectrum at the first time point and the intensity spectrum at the second time point by an average of signal intensities between the intensity spectrum at the first time point and the intensity spectrum at the second time point.

5. The biological analysis device according to claim 1, wherein the CPU calculates the change index in accordance with a degree of scattering of the signal intensity for each frequency in the plurality of intensity spectra.

6. The biological analysis device according to claim 5, wherein the CPU calculates the change index by dividing a standard deviation or a dispersion of the signal intensity for each frequency between the plurality of intensity spectra by the average of the signal intensities between the plurality of intensity spectra.

7. The biological analysis device according to claim 1, wherein:
the CPU calculates a blood pressure index related to the blood pressure of the biological body from the biological index.

8. A biological analysis method comprising:
determining a boundary between a first bandwidth in which a temporal change in a signal intensity is large and a second bandwidth which is located closer to a high frequency side than the first bandwidth and in which a temporal change in the signal intensity is less than the first bandwidth in a plurality of intensity spectra, within an intensity spectrum, related to frequencies calculated sequentially with regard to light reflected and received inside a biological body through radiation of a laser beam;
using the boundary to establish a frequency range in the intensity spectrum, the boundary being an upper limit of the frequency range;
calculating a biological index related to a blood flow of the biological body from a signal intensity within the frequency range; and
calculating a blood pressure P of the biological body according to Expression (4):

$$P = a_0 \frac{Q}{d^4} = \frac{a_0 \cdot a_2 \cdot F}{(a_1 \cdot M^{1/3})^4} = a \cdot \frac{F}{M^{4/3}} \quad (4)$$

$$(a = a_0 \cdot a_2 / a_1^4)$$

where P is the blood pressure, M is a blood quantity index obtained by integrating intensities in the intensity spectrum within the frequency range, F is a blood flow index obtained by integrating a product of an intensity of each frequency in the intensity spectrum and the frequency within the frequency range, a, $a_0$, $a_1$ and $a_2$ are constants, Q is a product of $a_0$, $a_2$ and F, and d is a product of a1 and $M^{1/3}$, wherein, in determining the boundary, the method further comprising:
calculating, sequentially, a change index which is an index of a temporal change quantity of the signal intensity for each frequency in the plurality of intensity spectra,
determining whether the change index at a frequency is less than a predetermined threshold, and
determining the frequency at which the change index is less than the predetermined threshold as the boundary.

9. A non-transitory computer readable medium having a program imbedded therein, the program, when executed by a computer, causing the computer to function as:
a CPU which:
determines a boundary between a first bandwidth in which a temporal change in a signal intensity is large and a second bandwidth which is located closer to a high frequency side than the first bandwidth and in which a temporal change in the signal intensity is less than the first bandwidth in a plurality of intensity spectra, within an intensity spectrum, related to frequencies calculated sequentially with regard to light reflected and received inside a biological body through radiation of a laser beam, uses the boundary to establish a frequency range in the intensity spectrum, the boundary being an upper limit of the frequency range,
calculates a biological index related to a blood flow of the biological body from a signal intensity within the frequency range, and
calculates a blood pressure P of the biological body according to Expression (4):

$$P = a_0 \frac{Q}{d^4} = \frac{a_0 \cdot a_2 \cdot F}{(a_1 \cdot M^{1/3})^4} = a \cdot \frac{F}{M^{4/3}} \quad (4)$$

$$(a = a_0 \cdot a_2 / a_1^4)$$

where P is the blood pressure, M is a blood quantity index obtained by integrating intensities in the intensity spectrum within the frequency range, F is a blood flow index obtained by integrating a product of an intensity of each frequency in the intensity spectrum and the frequency within the frequency range, a, $a_0$, $a_1$ and $a_2$ are constants, Q is a product of $a_0$, $a_2$ and F, and d is a product of a1 and $M^{1/3}$,
wherein, in determining the boundary, the CPU:
calculates, sequentially, a change index which is an index of a temporal change quantity of the signal intensity for each frequency in the plurality of intensity spectra,
determines whether the change index at a frequency is less than a predetermined threshold, and
determines the frequency at which the change index is less than the predetermined threshold as the boundary.

* * * * *